US011400176B2

(12) United States Patent
Kopperschmidt et al.

(10) Patent No.: US 11,400,176 B2
(45) Date of Patent: Aug. 2, 2022

(54) AUTOMATIC DISINFECTING MACHINE FOR DISINFECTING THE SKIN, AND METHOD

(71) Applicant: FRESENIUS MEDICAL CARE DEUTSCHLAND GMBH, Bad Homburg (DE)

(72) Inventors: Pascal Kopperschmidt, Dittelbrunn (DE); Pia Daniel, Bodman (DE); Reiner Spickermann, Wasserlosen-Burghausen (DE); Otto Arkossy, Budapest (HU); Cacilia Scholz, Schwalbach (DE); Kai-Uwe Ritter, Rednitz-Hembach (DE); Elke Schulte, Schweinfurt (DE); Christopher Hauke, Mainz-Kostheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 364 days.

(21) Appl. No.: 16/479,939

(22) PCT Filed: Jan. 29, 2018

(86) PCT No.: PCT/EP2018/052120
§ 371 (c)(1),
(2) Date: Jul. 23, 2019

(87) PCT Pub. No.: WO2018/138329
PCT Pub. Date: Aug. 2, 2018

(65) Prior Publication Data
US 2019/0374668 A1 Dec. 12, 2019

(30) Foreign Application Priority Data
Jan. 30, 2017 (DE) .................. 10 2017 201 441.5

(51) Int. Cl.
*A61L 2/00* (2006.01)
*A61L 2/24* (2006.01)
(Continued)

(52) U.S. Cl.
CPC ............... *A61L 2/24* (2013.01); *A01N 25/04* (2013.01); *A01N 31/02* (2013.01); *A01N 59/00* (2013.01);
(Continued)

(58) Field of Classification Search
CPC ........ A61L 2/0082; A61L 2/0088; A61L 2/16; A61L 2/20
(Continued)

(56) References Cited

U.S. PATENT DOCUMENTS 5,647,373 A   7/1997  Paltieli
5,863,497 A   1/1999  Dirksing
(Continued)

FOREIGN PATENT DOCUMENTS

CN   203841738 U   9/2014
CN   105102005 A   11/2015
(Continued)

OTHER PUBLICATIONS

International Search Report and Written Opinion issued in corresponding International Patent Application No. PCT/EP2018/052120 (with English translation of International Search Report) dated Jun. 5, 2018 (17 pages).
(Continued)

*Primary Examiner* — Monzer R Chorbaji
(74) *Attorney, Agent, or Firm* — Kilyk & Bowersox, P.L.L.C.

(57) ABSTRACT

The invention relates to a method and an automatic disinfection machine for the controlled disinfection of the skin of a patient comprising a treatment chamber for accommodat-
(Continued)

ing the body part with the skin to be disinfected; an electrically controllable disinfecting device for disinfecting the skin, a recording device for recording the disinfection of the skin in the form of disinfection data, a data processing control device for controlling the disinfecting device and the recording device. The control device is thereby designed to effect the disinfection of the skin by controlling the disinfecting device, record the disinfection of a skin section of the skin in the form of disinfection data by controlling the recording device.

15 Claims, 9 Drawing Sheets

(51) Int. Cl.
| | |
|---|---|
| *A61M 1/36* | (2006.01) |
| *A61B 90/80* | (2016.01) |
| *A01N 25/04* | (2006.01) |
| *A01N 31/02* | (2006.01) |
| *A01N 59/00* | (2006.01) |
| *A01N 59/12* | (2006.01) |
| *A61B 17/34* | (2006.01) |
| *A61L 2/28* | (2006.01) |

(52) U.S. Cl.
CPC .......... *A01N 59/12* (2013.01); *A61B 17/3476* (2013.01); *A61B 90/80* (2016.02); *A61L 2/0088* (2013.01); *A61L 2/28* (2013.01); *A61M 1/3655* (2013.01); *A61M 1/3661* (2014.02); *A61L 2202/14* (2013.01)

(58) Field of Classification Search
USPC .................................................. 422/28, 292
See application file for complete search history.

(56) References Cited

U.S. PATENT DOCUMENTS

| | | | |
|---|---|---|---|
| 9,006,976 | B2 | 3/2015 | Watson et al. |
| 2006/0118039 | A1* | 6/2006 | Cooper ................. A61M 35/25 |
| | | | 118/696 |
| 2007/0015552 | A1 | 1/2007 | Bolling |
| 2010/0303671 | A1 | 12/2010 | Bertrand |
| 2013/0215245 | A1 | 8/2013 | Haidegger et al. |
| 2013/0226073 | A1 | 8/2013 | Kummerfeld et al. |
| 2014/0271355 | A1 | 9/2014 | Mason |
| 2015/0065916 | A1 | 3/2015 | Maguire et al. |
| 2015/0151012 | A1 | 6/2015 | Ritz |
| 2016/0220714 | A1 | 8/2016 | Weltmann et al. |
| 2016/0249990 | A1 | 9/2016 | Glozman et al. |
| 2017/0035335 | A1 | 2/2017 | Breteau et al. |

FOREIGN PATENT DOCUMENTS

| | | |
|---|---|---|
| DE | 102012003563 A1 | 8/2013 |
| EP | 0913681 A2 | 5/1999 |
| JP | 2001282931 A | 10/2001 |
| WO | 2005093681 A1 | 10/2005 |
| WO | 2010029521 A2 | 3/2010 |

OTHER PUBLICATIONS

International Preliminary Report on Patentability issued in corresponding International Patent Application No. PCT/EP2018/052120 dated Aug. 8, 2019 (10 pages).
Common Knowledge Evidence (Clinical Skin Surgery, Lv Renrong et al, Shandong Science and Technology Press Jul. 31, 2014).
Office Action issued in corresponding Chinese Patent Application 201880009319.7 dated May 16, 2022 (English translation only) (14 pages).

* cited by examiner

AUTOMATIC DISINFECTING MACHINE FOR DISINFECTING THE SKIN, AND METHOD

This application is a National Stage Application of PCT/EP2018/052120, filed Jan. 29, 2018, which claims priority to German Patent Application No. 10 2017 201 441.5, filed Jan. 30, 2017.

The present invention relates to an automatic disinfection machine for the controlled disinfection of the skin of a patient and a method for the controlled disinfection of the skin of a patient.

The automatic disinfection machine according to the present invention is a medical treatment apparatus. Disinfecting the skin of a patient is mandatory in the course of many medical tasks, in particular prior to invasive patient treatments. To disinfect, medical personnel apply a disinfectant to the skin. In the process, it is left to the individual performing the disinfecting to disinfect the area of the skin with the provided disinfectant based on their knowledge. Thus, among other factors, the result of such a disinfection in particular depends on the individual performing it.

Medical treatment apparatus which automatically apply disinfectant to the skin are known. WO 2010/029521 A2 describes a treatment apparatus, in particular a cannulation robot, in which spraying the skin with a liquid disinfectant is regarded as being a suitable method of automatic disinfection. It is thereby not taken into account that the success of the disinfection depends on different factors. Even an automatic spraying of disinfectant will, depending on the environmental conditions, the condition of the sprayer, the disinfectant and the treated individual, yield a number of unacceptable disinfection results. Therefore, under the law of statistics, a corresponding number of medical complications will arise in the course of using such machines. This will create corresponding follow-up treatment costs for the attending physician and the hospital using the machine. In practice, when using such machines, either great efforts are expended for maintenance and inspection or, despite the automated disinfection, one resorts to manual disinfection for safety reasons. Given this situation, an efficient technical solution for safely disinfecting the skin of a patient is desirable.

The present invention is based on the task of specifying an apparatus and a method for efficiently and safely disinfecting the skin of a patient.

The invention solves this task by an automatic disinfection machine in accordance with the teaching of independent claim 1 and a method in accordance with the teaching of independent claim 15. Preferential embodiments, further developments or variants in particular constitute the subject matter of the independent claims. The subject matter of the claims is expressly made a part of the specification disclosure.

The inventive automatic disinfection machine for the controlled disinfection of the skin of a patient comprises:
- a treatment chamber to accommodate the body part with the skin to be disinfected;
- an electrically controllable disinfecting device for disinfecting the skin,
- a recording device for recording the disinfection of the skin in the form of disinfection data,
- a data processing control device for controlling the disinfecting device and the recording device;

wherein the control device is designed to effect the disinfection of the skin by controlling the disinfecting device and record the disinfection of an area of skin in the form of disinfection data by controlling the recording device.

Skin is automatically disinfected by the automatic disinfection machine according to the invention. The recording device of the automatic disinfection machine enables controlling the disinfection and thus provides safety during the use of the automatic disinfection machine. The disinfection of a predetermined section of the skin is recorded, the overall patient-individual nature of a body part therefore has less influence in the analysis. Disinfection control is thereby standardized and the results able to be better reproduced and compared. The disinfection itself can be more efficiently performed since by focusing on the section of skin, expenditures in terms of materials and time for the disinfection can be reduced and optimally adapted to the requirements of the medical treatment to be performed. For example, in the case of a subsequent cannulation of the disinfected skin, only a relatively small section of sterile skin is required for cannula insertion, in particular when the process can rely on the precision of a cannulation robot.

The skin section, in particular its size and shape, is in particular predetermined by the disinfecting action as locally applied to the skin and/or by a locally limited recording area or analysis area of disinfected skin and/or by other instrument-based means which will be described farther below. The size of the skin section can be limited to a few square centimeters, in particular to 0.5 to 10 $cm^2$ or 0.5 to 20 $cm^2$. In addition, however, the size of the skin section can also be selected from the preferential ranges of 0.5 to 100 $cm^2$, 1.0 to 100 $cm^2$, 1.0 to 50 $cm^2$, 5.0 to 50 $cm^2$, 5.0 to 30 $cm^2$.

The disinfecting device preferably comprises a dispensing device for a for a disinfectant, in particular for a liquid disinfectant. The disinfectant can be transparent and/or can be colored. A transparent disinfectant can be detected on the skin for example by measuring a coating thickness or by measuring optical parameters such as "reflectivity" or "gloss." The disinfectant can thereby be augmented with reflectivity-enhancing agents, e.g. reflecting particles. A colored disinfectant can be detected by colorimetric recording and in particular differentiated from the uncolored background—the color intensity is thereby a measure of the concentration or of the coating thickness respectively. Fluorescent dyes in the disinfectant enable detection as a function of the suitable excitation light. Since, in the ideal case, only the fluorescent dyes emit radiation in the emission frequency band; good contrast can be obtained—here as well, the measured intensity is a measure of the concentration of the dye or of the coating thickness.

Preferably, the dispensing device is a spray device which in particular comprises a multi-tip nozzle or an aerator. The spray device directs the dispensing of the liquid disinfectant onto the skin, in particular within a defined spatial angle. The dimensions of the disinfected skin section can thus be specified and the volume of disinfectant used for the disinfection efficiently dispensed. It is also possible and preferential for the dispensing device to have a single nozzle and/or in particular be configured to dispense the liquid disinfectant from the single nozzle and/or dispense it at excess pressure or without excess pressure, in particular one drop at a time. The dispensing device can comprise a pump device in order to transport the disinfectant and/or discharge it under pressure. The dispensing device can also be configured to allow the disinfectant to flow out under gravitational pull.

Preferably, the automatic disinfection machine comprises a liquid disinfectant or can be filled with a liquid disinfectant. The liquid disinfectant can be a solution, in particular an aqueous solution. The solution can comprise at least one dissolved additive, in particular a germicide. The additive can in particular be an oxidizing agent, a phenol derivative, a carbonyl compound or a halogen, or can contain a mixture of such substances. The additive can in particular be an alcohol, in particular ethanol, or hydrogen peroxide or iodine.

Preferably, the control device is designed to automatically apply a predetermined dosage of disinfectant on the section of skin to be disinfected. The disinfectant dosage is regulated by the control device, preferably by adapting the duration of application and/or the total amount of disinfectant used per time during the application.

It is also possible and preferential for the disinfecting device to comprise an application device by means of which the disinfectant can be applied directly onto the skin section, in particular dispense same without the formation of drops and in particular continuously. The application device can comprise an application section which dispenses the disinfectant; same can be configured as a plunger able to be replenished or saturated respectively with the disinfectant which comes into direct contact with the skin section in order to disinfect said skin section. The plunger section can thereby be a consumable item loaded automatically by the automatic disinfection machine or manually. The application section can also be designed to apply the disinfectant without being in direct contact with the skin in particular by the application section always being held at a minimum distance from the skin. This can be realized for example by means of a sensor, in particular by optical measurement or by an electrical impedance sensor.

It is also possible and preferential for the disinfecting device to be configured with a disinfecting gas for disinfection. To that end, the disinfecting device can comprise a compartment able to be filled with gas which closes—in particular in gas-tight manner—when pressed against the skin or is held at an—in particular minimum—distance from the skin. The disinfecting device preferably comprises a retention device for holding and in particular guiding the compartment, preferably a drive device for moving a movable retention device. The gas can for example be hydrogen peroxide which can be provided from a storage container of the automatic disinfection machine. Preferably, the control device is designed to automatically apply a predetermined dosage of gas onto the section of skin to be disinfected. The gas dosage is regulated by the control device, preferably by adapting the duration of application and/or the concentration of gas.

It is also possible and preferential for the disinfecting device to be designed to disinfect with a disinfecting plasma, in particular cold plasma. Cold plasma is in particular obtained directly from the surrounding atmosphere and contains reactive radicals which, in conjunction with low ultraviolet radiation, destroy bacterial cell walls or virus coats respectively. To that end, the automatic disinfection machine, in particular the disinfecting device, can comprise a plasma generating device which can in particular be realized by thin layer technology or surface micro-discharge technology, as described for example in U.S. Pat. No. 9,006,976 B2, in order to keep the necessary physical volume and energy consumption low. In particular, the disinfecting device can additionally comprise a UV radiation source for irradiating the skin section at doses harmless to the skin. Additionally, the disinfecting device can comprise a compartment able to be filled with the plasma which closes—in particular so as to be gas-tight—when pressed against the skin or is held at an—in particular minimum— distance from the skin. The disinfecting device preferably comprises a retention device for holding and in particular guiding the compartment, preferably a drive device for moving a movable retention device.

Preferably, the control device is designed to automatically apply a predetermined dosage of plasma on the section of skin to be disinfected. The plasma dosage is regulated by the control device, preferably by adapting the duration of application and/or the plasma composition and/or ion concentration. Further details are known on realizing plasma disinfection of the skin, see for example WO 2015/032888 A1.

It is also possible and preferential for the disinfecting device to be configured to—in particular solely—irradiate the skin section with germicidal radiation. Preferably, the disinfecting device comprises a radiation device for irradiating the skin section with radiation, which in particular comprises at least one radiation source. Preferably, two or three sources of radiation are provided, or multiple sources of radiation are arranged on the radiation device at an offset from one another. Preferably, the arrangement is configured such that the radiation is directed substantially perpendicular to the section of skin to be radiated. In addition, however, one or more radiation sources can be arranged and/or disposed and/or aligned such that at least one of the radiation sources radiates its radiation onto the skin section in one—or more—direction(s) deviating from the perpendicular, in particular at an angle $\alpha$ between $20°<=\alpha<=85°$. Doing so can thus achieve homogeneous irradiation, also in the case of varying skin topography.

The source of radiation can in particular be a UV radiation source or UV light source, in particular an LED. The source of radiation can be configured to emit UV radiation in the UV-B spectrum. Preferably, the UV radiation source is configured to emit UV radiation in the UV-C spectrum, since this radiation is particularly harmless to the skin and therefore easily dosed. The UV range of electromagnetic radiation spans the wavelengths of 1 nm to 400 nm of the spectrum, in particular 100 nm to 380 nm. UV-B designates the 315-280 nm wavelengths, UV-C designates the 100-280 nm wavelengths. Preferably, the automatic disinfection machine, in particular the disinfecting device, is designed to activate the radiation source to emit radiation of selectable intensity. The radiation dosage can thus be made application-dependent, in particular in consideration of the skin type as can be known from the patient data or entered via user input or which the automatic disinfection machine can measure by e.g. colorimetry.

The source of radiation can be designed to emit radiation, in particular visible light, can in particular be an LED, and can in addition be designed to support the recording of the disinfectant applied to the skin section, in particular by means of optical detection or radiation detection respectively.

Preferably, the radiation device comprises a beam guiding device in order to form the radiation radiated onto the skin section, in particular so as to use the shape of the beam to define the dimensions of the disinfected skin section. The beam guiding device can comprise at least one of the following components: a shutter, in particular a controllable aperture-variable shutter; in particular a frame shutter for two-dimensional framing of the radiation cone; a lens for forming, directing, parallelizing or focusing the beam; a reflector, in particular a semipermeable reflector; a prism; a controllable gate for interrupting the beam.

Preferably, the control device is designed to automatically radiate a predetermined radiation dosage onto the skin section to be disinfected. The control device preferably regulates the radiation dosage by adapting the radiation duration and/or radiation intensity.

According to one first preferred embodiment, the recording device comprises a sensor device by means of which a measurement characterizing the disinfection quality can be made of the disinfected skin section.

The disinfection quality can in particular be determined by determining the portion of the surface of the skin section encompassed by the disinfecting action and in particular wetted by a disinfectant. To that end, the control device comprises algorithms, by means of which the measurement is analyzed in the manner cited and/or in another manner.

Preferably, the recording device is a component part of the disinfecting device or is preferably arranged, in particular mounted, on the same retention device on which the disinfecting device is also arranged, in particular mounted. The recording can thereby be made in particular without any time delay and at substantially the same position at which the disinfecting device was previously disposed for the purpose of disinfection. This can in particular be a position at which the disinfecting device is disposed substantially perpendicularly above the section of skin to be disinfected. In particular, the retention device can be movable and the control device can move same in an automated manner in order to position the disinfecting device and/or the recording device in the target position for disinfecting and/or recording.

Preferably, the automatic disinfection machine, or the treatment apparatus contained therein, comprises a retention device, by means of which the disinfecting device and/or the recording device is held over the skin section. Said retention device is preferably movable and an electric motor device is in particular provided, by means of which the movement of the retention device can be driven and/or controlled. Preferably, the control device is designed to control the movement of the movable retention device. Preferably, the movable retention device is an articulated arm or a rail system of components connected by rails arranged oppositely movable to each other on at least one rail.

The sensor device is preferably a radiation detecting device comprising at least one radiation sensor, in particular with spatial resolution. This is advantageously a radiation sensor enabling a spatially resolved image of the radiation incident thereon. The radiation sensor can for example comprise an image capture device, in particular a CCD or CMOS chip or a camera or the like.

Preferably, the radiation detecting device comprises at least two, three or multiple radiation sensors which are arranged at a spacing from one another and preferably arranged and/or disposed and/or aligned so as to be able to detect radiation from different directions. Doing so enables reliable measurements, in particular also of varying skin topographies.

Preferably, the radiation detecting device is designed to capture a three-dimensional image of the skin section. To that end, the radiation detecting device preferably comprises two or three radiation sensors which pick up radiation from different spatial directions. The x-y plane of a Cartesian coordinate system can thereby substantially be the plane of the skin section, a first radiation direction can preferably lie in the x-z plane and enclose an angle $\alpha$ to the z-axis, a second radiation direction can preferably lie in the x-z plane and enclose an angle $\alpha$—preferably the same angle $\alpha$—to the z-axis, and a third radiation direction can run parallel to or coincide with the z-axis, thus be arranged substantially perpendicularly above the skin section. The capturing of a spatial image can be used during the analyzing of the disinfection data after a liquid disinfectant has been applied so as to factor in the influence the skin topography of the skin section has on the disinfection quality and/or disinfection variable to be determined. This thereby enables compensating for the influence of the patient/patient condition-dependent skin surface structure and more objectively calculating the disinfection variable. Angle $\alpha$ is preferably between $20°<=\alpha<=85°$.

The radiation detecting device can be configured such that at least one component as described above of a beam guiding device is arranged between the radiation source and radiation sensor, thereby improving the measurement.

Preferably, the recording device comprises at least one source of radiation by means of which the skin section can be irradiated. The radiation emitted by the at least one radiation source and reflected and/or scattered by the skin section is preferably measured by the radiation detecting device.

The recording device provided with a radiation source can thereby be used to optically measure the coating thickness of a layer of disinfectant applied to the skin section, in particular employing confocal optics or, respectively, optics with movable focus distance detection and a reflectivity measurement at the boundary surfaces detected by intensity measurement.

Preferably, the control device is designed to evaluate at least one first image of the disinfected skin section by suitable control device algorithms obtaining statistical information on the disinfection quality contained in the disinfection data as image data. This statistical information can be a mean brightness value, in particular dependent on the wavelength and/or wavelength band of the radiation emission of the coloring or fluorescent dye which can be contained in the disinfectant. The statistical information can be the mean intensity of the radiation which is reflected from the skin by the wetting and reflecting disinfectant but not from the skin which is not wetted and therefore non-reflective as measured in a reflection measurement.

Preferably, the control device is designed to evaluate at least one first image of the disinfected skin section by digital processing control device algorithms obtaining information on the disinfection quality contained in the disinfection data as image data. In particular, outliers are thereby eliminated, artifacts identified and eliminated, image noise eliminated, or, by allowing for threshold(s), such regions of the image having similar properties differentiated. In particular, a disinfection variable can be determined in which the influence of the skin topography has been neutralized by the calculative consideration of the spatially-resolved detected intensity data (see above) and the spatially-resolved skin topography data.

Preferably, the control device is designed to obtain at least one disinfection variable characterizing the disinfection quality from an image of the disinfected skin section. The disinfection variable can be stored as disinfection data in a data storage device of the automatic disinfection machine or another data storage device, in particular as a function of patient data of the patient whose skin section was disinfected. The disinfection data can again be factored in when analyzing the disinfection control as carried out by means of the recording device, in particular to compare historical (previously determined) data to the currently obtained data.

Preferably, the control device is designed to record at least one first image of the skin section to be disinfected, thus prior to the disinfection being performed, and at least one second image of the disinfected skin section, thus after the disinfection has been performed, and in particular determine the disinfection quality, in particular the at least one disinfection variable, by calculative comparison of the images. The calculative comparison can in particular be a pixel-by-pixel mathematical operation, in particular a subtraction, of image properties, in particular brightness or intensity in a specific color channel of a polychromatic image.

Preferably, the control device is additionally designed to record, and in particular save, at least one image during the disinfection, in particular an image of the skin section to be disinfected, thus enabling the disinfection process to be documented.

Preferably, the automatic disinfection machine, in particular its control device, is additionally designed to store the at least one disinfection variable, in particular as a component of disinfection data, and thus document the disinfection performed of the patient's skin section, in particular as a component of certificate data. The generating of certificate data is preferably provided for with the automatic disinfection machine, and preferably with a treatment apparatus, in particular a cannulation robot, containing the inventive automatic disinfection machine as a component part or module. The certificate data can furthermore hold patient data, e.g. vascular structure data on the course of subcutaneous vessels, particular the course and/or condition of an arteriovenous fistula. The certificate data can also contain data on the automatic treatment performed at the disinfected skin section, e.g. treatment data on an automated cannulation performed by the cannulation robot at the disinfected skin section as obtained during or subsequent the treatment, e.g. the treatment-induced changes to the vascular structure in the form of current vascular structure data, or data on the success and details of the priming of the intracorporeal and extracorporeal fluid system, in particular connecting the fluids in the blood vessel, the cannula and any connected tubes or containers there may be so as to be free of air bubbles. The generating and providing of certificate data is particularly highly advantageous in automated processes since same may be needed to supplement or replace clinical notes, in particular an automatically generated electronic physician's report. Production of a computer-generated protocol is an essential condition for the subsequent reproducibility of the disinfection and/or treatment performed. Other parameters can also be saved in such protocol data by the recording apparatus, in particular status information supplied by individual components of the automatic disinfection machine, e.g. diagnostic program results, information on the filing level, age or other properties of the filler material, component serial numbers and/or maintenance information.

Preferably, the automatic disinfection machine, in particular its control device, and in particular the method according to the invention, are designed to implement a normed or respectively standardized disinfection procedure in which a predetermined dosage of a disinfecting measure, in particular a dosage of radiation, a volume of liquid, a dosage of gas or a dosage of plasma is applied onto a section of skin of predetermined dimension, in particular predetermined surface size and form, particularly within a predetermined time interval, by means of the disinfecting device. In this normed or respectively standardized disinfection procedure, at least one disinfection variable characterizing the disinfection quality is additionally determined according to a predetermined method by means of the recording device and provided in the form of disinfection data. Utilizing such a normed or respectively standardized disinfection procedure allows a better comparison of disinfection results from patient to patient and over the course of recurring disinfections and treatments.

The reproducibility and safety of the disinfection and subsequent treatments are thus improved.

In accordance with a second preferred embodiment, the recording device comprises a sensor device by means of which a measurement characterizing the disinfection quality can be made on the recording device, in particular, however, not on the skin section. This embodiment can also be combined with the first preferential embodiment. One advantage of the second preferred embodiment lies in dispensing with the evaluation of the disinfection data, in particular image data, obtained from the skin section, which is necessary in the case of the first embodiment, in particular the visual recording of the skin section. The reference to data obtained of the recording device itself can be more precise and reliable since the influence of the patient-individual skin shape does not come into play.

Preferably, the recording device comprises a detection device, in particular a sensor device, by means of which at least one disinfection parameter characterizing the operation of the disinfecting device is queried at least once during the automatic disinfection and saved, preferably repeatedly queried and saved. The disinfection parameter can in particular characterize the operations executed or the energy consumed or a total input power. For example, the disinfecting device can comprise an electric motor or an electric pump which allows measuring the electrical energy related to its operation, i.e. the power consumption, or which can output information on the power consumption via a connection, in particular a data connection, and in particular to the control device. The proper operation of the disinfecting device can be concluded from such data.

Preferably, the control device is designed to determine the operability of the at least one sensor of the detection device by means of a diagnostic procedure and/or calibrate the at least one sensor of the detection device by means of a program-controlled calibration procedure. This applies to the first and second preferential embodiment of the automatic disinfection machine. The disinfection data can contain information on the results of such procedures, in particular in certificate data.

The sensor device can comprise at least one sensor which is arranged during the implementation of the disinfection by the disinfecting device so as to measure the disinfecting action, in particular in place of the skin or the skin section shielded by the sensor. To that end, the at least one sensor can be arranged in the stream of the disinfectant or in the path of the electromagnetic radiation beam or in the effective range of a gas or plasma disinfecting device. In addition, the recording device can comprise at least one retention device by means of which the at least one sensor is arranged as desired. In particular, the at least one sensor can also be arranged adjacent the section of skin to be disinfected or adjacent the skin at said skin section. The sensor can for example be an impedance sensor with which a thickness of a coating of disinfectant deposited on the impedance sensor can be measured. The sensor can also be a photodetector with which a dosage of radiation radiated toward the skin section during disinfection can be measured.

Preferably, the sensor device comprises at least one sensor by means of which a disinfectant discharged from the disinfecting device is detected, by means of which a radiation intensity emitted from the disinfecting device is detected, by means of which a gas or plasma concentration is detected, whereby in particular the respective time at which the disinfecting action occurred is also detected. The control device is to that end preferably designed to determine at least one disinfection variable characterizing the disinfection by means of the cited disinfection parameter.

The control device, the automatic disinfection machine respectively, also preferably exports the disinfection data generated by the automatic disinfection machine pursuant to the second preferential embodiment as a component of certificate data and in particular saves same, in particular in a data storage apparatus of the data processing system, the networked component of which can be the automatic disinfection machine.

The control device is preferably designed to analyze the disinfection data in consideration of at least one criterion and in particular indicate the quality of the disinfection by means of a disinfection variable determined from disinfection data pursuant to the at least one criterion. In particular, whether a performed disinfection is acceptable or not can thus be determined.

The criterion can allow for the comparison of a disinfection variable to at least one predetermined reference value so as to enable categorizing of the disinfection quality determined in the form of the disinfection variable.

The control device is preferably designed to re-disinfect the same section of skin as a function of the disinfection data and in consideration of at least one criterion by controlling the disinfecting device, in particular as a function of the disinfection variable. An unacceptable disinfection result can in particular thereby be improved.

The control device is preferably configured to obtain a predetermined disinfection variable via regulation. The predetermined disinfection variable is thereby the target value of the regulation, an operating parameter of the disinfecting device, in particular a disinfection period, a disinfectant volume and/or a disinfection intensity serving as the actuating variable of the regulation and the disinfection variable to be repeatedly determined from the disinfection data is the control variable of the regulation. The control variable can thereby be particularly accurately set.

Preferably, the disinfecting device comprises a skin manipulating device by means of which the skin section can be moved while the body part with the skin section is immovable and/or fixed. Preferably, the skin manipulating device comprises at least one or at least two movable contact sections, by means of which the skin is stretched. One contact section, in particular multiple or all, can be disposed on a movable, in particular flexible arm of the skin manipulating device. The disinfecting device and/or the recording device can be disposed and/or mounted on the skin manipulating device. Thus, both the disinfection as well as the recording can occur under a manipulated skin condition, e.g. on stretched skin. The skin manipulating device is regarded as being advantageous due to disinfection and/or recording being able to be standardized from patient to patient by tightening the skin to a predetermined measure or can also then be standardized when a change in the skin topography occurs during the course of a series of recurring disinfections/treatments for in particular chronic illnesses. The disinfection and its control is thereby made more reliable and reproducible.

The disinfecting apparatus, in particular the control device, is preferably additionally designed to run the disinfection prior to, during and/or subsequent the skin manipulating device moving the skin. This thereby effects a particularly high exposure of porous skin surface and thus an efficient disinfection of the skin surface. The disinfecting apparatus, in particular the control device, is preferably additionally designed to run the recording prior to, during and/or subsequent the skin manipulating device moving the skin. This thereby effects a particularly high exposure of porous skin surface and thus a reliable recording of the surface of the skin.

The puncturing of blood vessels, also known as cannulation, is a routine procedural step in the medical treatment of many patients in which a fluid connection, in particular a cannula, is established between a patient's blood circulation and an external fluid system. Cannulation is usually performed by physicians or trained personnel. The quality of the vascular access created by the cannulation thereby depends on a plurality of parameters, which are in particular affected by the individual and temporally varying abilities of the medical personnel and the physical characteristics of the patients to be treated as well as the diversity of the technical instruments used in cannulation.

Being a routine procedure in many treatments, cannulation is also frequently performed. In order to thereby standardize cannulation, make efficient use of financial as well as personnel resources, and reliably ensure high treatment quality, cannulation robots have been developed which autonomously perform a cannulation procedure on patients using suitable sensor technology and motor function. Such cannulation robots and the technical resources thereby used are known from e.g. EP 0 654 244 B1, US 2015/0065916 A1 and WO 2015/052719 A1.

The automatic disinfection machine preferably comprises a base on which preferably all of the components of the automatic disinfection machine are mounted, in particular the data processing control device, the disinfecting device and the recording device. If the automatic disinfection machine is a component part of a treatment device, e.g. a cannulation robot, the base of the automatic disinfection machine can be a component part of the treatment device.

The treatment chamber can be a partly enclosed or open spatial area which can in particular be integrated into a treatment apparatus, in particular a cannulation robot. The treatment chamber serves to at least partly accommodate the part of the patient's body with the subcutaneous blood vessel to be detected. The body part is preferably an arm or a leg.

The treatment chamber preferably comprises a supporting device for supporting the body part, in particular a rest or a plurality of rests.

The automatic disinfection machine preferably comprises a fixation device, by means of which the patient's body part containing the skin section, in particular an arm or a leg, is immobilized in the treatment chamber. This thereby enables an even better defining of the position of the skin section to be disinfected by the automatic disinfection machine, with the disinfection becoming more reliable, of better reproducibility and of better comparability patient to patient. The fixation device can comprise at least one retaining strap, retaining bracket, retaining cuff, in particular a cuff able to filled with a fluid and thereby pressure-variable, as will be described further in the following. The automatic disinfection machine, in particular its control device, is preferably designed to automatically control the fixation device and carry out the fixation once the patient's body part is disposed in the treatment chamber.

The treatment chamber can comprise a fixation device, by means of which the body part can be immobilized relative to the treatment chamber or relative to the supporting device and is immobilized during the disinfection and/or subsequent treatment, in particular cannulation. The fixation device can comprise at least one fixation strap for securing the body part to the supporting device. The fixation device can furthermore also assume the function of the supporting device, by for example the fixation device suspending the body part in the treatment chamber. The fixation preferably ensues so as to restrict the translational and/or rotational mobility of the body part in at least one, at least two, three, four, five or six spatial directions, preferably in all six spatial directions in positive and negative direction along the three orthogonal spatial axes of a Cartesian coordinate system and/or all six rotational directions around said spatial axes.

The fixation device can comprise or be formed by a cushion device. The cushion device can be designed to accommodate a fluid, in particular air, a liquid or a gel. Preferably, an electrically controllable fluid transport device can be provided to transport the fluid, in particular a pump or a pressing device. This transport is preferably automatically controlled by the control device such that the detection apparatus can preferably automatically perform the fixation. In the fixation process, it can be provided for the fluid transport device to increase the volume of fluid in the cushion device so as to restrict the mobility of the body part disposed on the cushion device and preferably immobilize same. The cushion device can partly or completely encircle the body part; in particular, the cushion device can be designed as a closed or open hose ring, similar to a cuff as used in measuring blood pressure. The cushion device serving as a supporting or fixation device is thereby preferably fixed in the detection apparatus. The disinfecting device and/or the recording device is/are preferably integrated into the fixation device.

The fixation device can further comprise one or more movable clamping arms which can be movably mounted in the treatment chamber, in particular movably mounted on the supporting device or fixation device. The one or more movable clamping arms can preferably be moved by one or more actuator devices of the fixation device in order to achieve the desired immobilizing of the body part.

Moreover, the fixation device, in particular the fixation device comprising at least one retaining clamp, can be configured to apply a tension to the skin with the subcutaneous blood vessel to be disinfected by the fixation device or the clamping arms having adhesive contact points which make contact with and adhesively hold the skin so that a pulling motion of the retaining clamps tautens the skin positioned between the contact sections of the retaining clamps. This can thereby immobilize the blood vessel in the skin to be disinfected. On the other hand, its position can be manipulated by moving the retaining clamps adhering to the skin. The contact sections can effect the adhesion particularly by means of a friction-inducing material applied to the contact section, e.g. silicone elastomer, or by an adhesive section applied to the contact section.

The pressing device can furthermore comprise a movable manipulation device, in particular a holding device for a tool, e.g. a robotic arm, by means of which a pressing head serving as a tool is placed onto the body part and the desired pressure exerted. The contact area of the pressing head can in particular amount to between one and several square centimeters so that a relatively localized pressure can in particular be applied to the body part. Thus, in particular only one single blood vessel or a smaller number of blood vessels can be stemmed to the desired extent, thereby enabling gentle treatment. The contact area can additionally comprise a force sensor in order to be able to control the contact pressure thereto—additionally to the measurement provided by the vascular structure measuring device. The contact area can amount in particular to between 1 cm$^2$ and 100 cm$^2$, particularly between 1 cm$^2$ and 50 cm$^2$, preferentially between 1 cm$^2$ and 10 cm$^2$.

The pressing device can comprise a force sensor for measuring the contact pressure. The value of the contact pressure, in particular that which exists when the patient blood vessel to be detected reaches the desired—position and/or dimension-characterizing—value, can be stored in a data storage device. The data storage device can be a part of the detection apparatus or a part of the treatment apparatus, in particular the cannulation robot comprising the detection apparatus.

Preferably, the pressing device is designed to not exceed a predetermined maximum contact pressure value. This value can be determined beforehand as being the value at which the blood flow of the stemmed blood vessel is fully obstructed or restricted up to a certain value. Doing so treats the patient's body part with care. This safety device can be particularly advantageous with dialysis patients or those with other illnesses in which a blood vessel, in particular an arteriovenous fistula, needs to be punctured repeatedly and can thus be particularly sensitive to pain.

Preferably, the detection apparatus comprises a blood pressure measuring device. The pressing device can be configured as a blood pressure measuring device.

Preferably, the contact pressure is set to a value of between 40 mmHg and 100 mmHg. The contact pressure is preferably selected so as to interrupt the venous outflow through the blood vessel to be detected but not, however, the arterial inflow. It is therefore preferential for the contact pressure to be lower than the diastolic pressure.

The pressing device can be designed to repeatedly apply contact pressure, in particular by means of a contact section of the pressing device repeatedly pressing against the body part. Percussing the body part releases histamine in the skin, which leads to reddening of the skin, whereby the blood vessel(s) dilate. This manipulation also enables a better depicting of the blood vessel.

The vascular manipulation device can be designed as a heat transfer device in order to transfer warmth to the patient's body part. Warmth can improve circulation in the skin. Warmth can dilate a vessel such that a subsequent treatment, in particular an automatic cannulation, can be improved. The vascular manipulation device can in particular comprise a thermal transfer section provided to contact the skin and transfer warmth by diffusive heat transport. As described above, a cushion device can be configured as a heat transfer device by the fluid medium inside the cushion device being heated or cooled to a target temperature. The cushion device can in particular be designed as a sleeve, particularly a cuff, so that the sleeve at least partly or completely encircles the body part in at least one plane, particularly in tube-like form. Doing so can thereby achieve a particularly large-area thermal contact with the skin in order to stimulate blood circulation over a large area of tissue. Optionally, the sleeve can be inflated or respectively expanded with fluid in order to exert a contact pressure able to serve in stemming the blood flow and which can on the other hand improve thermal contact between the sleeve and the body part. The sleeve can be transparent and/or comprise a gap or opening to enable measuring by the vascular structure measuring device. The heat transfer device can in particular comprise at least one temperature control device, and preferably at least one temperature sensor, and in particular be designed to set the temperature in regulated manner.

Preferably, the heat transfer device comprises a radiant heater in order to transfer warmth to the body part by radiation. The radiant heater can be an infrared radiant heater. The radiant heater can be designed to radiate the heat directed at a body part.

Preferably, the control device is designed to perform the disinfection and/or the recording within a predetermined time interval, in particular a time interval of less than 60 seconds, preferably less than 30 seconds, preferably less than 20 seconds, preferably less than 10 seconds, preferably less than 5 seconds, preferably less than 1 second.

Preferably, the automatic disinfection machine according to the invention or one of its embodiments described herein is a component part of a treatment apparatus, in particular a cannulation robot. The cannulation robot, respectively the control device of the cannulation robot, is thereby preferably designed to automatically perform the cannulation of the skin section disinfected under the control of the automatic disinfection machine. A treatment apparatus can further carry out a non-invasive treatment of the blood vessel.

The automatic disinfection machine, respectively its control device, can be designed to access stored patient data—particularly in a patient database—in order to determine information on past manipulation data, particularly control variables of the disinfection, e.g. disinfection parameters. A cannulation robot can be designed to determine suitable cannulation procedural steps in the cannulating of the patient's blood vessel from such patient data (historical data), and preferably determine the cannulation to be performed, in particular the program parameters used in the program-controlled automatic cannulation, as a function of said historical data. Such historical data contains in particular the position of one or more of the patient's skin sections as previously disinfected with the automatic disinfection machine, and which is in particular available as patient data. Such historical data in particular contains information on the position and condition of prior puncture sites on the patient's body part which is in particular available as patient data.

The automatic disinfection machine can comprise a detection apparatus and be designed to perform an identification of the suitable subcutaneous blood vessel in the patient's body part for treatment, and in particular select a suitable insertion point on the skin for puncturing said blood vessel and, on the basis of same, also determine the position of the skin section to be disinfected which typically evenly surrounds the puncture site. The identification can be made for example in a control device via program-controlled analysis of an image obtained by the vascular structure measuring device equipped with an imaging sensor or the recording device.

In the sense of the invention, a "cannula" is a tubular body, in particular a rigid or flexible injection needle, having a lumen of a geometry and external dimensions suited for use in cannulation of a blood vessel. Preferably, the cannula comprises a hollow needle and a connector part.

The potential advantages as well as embodiments, further developments or variants of the invention cited previously also apply accordingly to the inventive cannulation robot.

A cannulation robot is an apparatus which automatically; i.e. at least intermittently or continuously, performs at least one cannulation process step in a patient blood vessel, or several or all intended process steps, without the intervention of a human operator, e.g. medical personnel. This thereby ensues in particular by the program parameters of the automated cannulation being accordingly selected by the system and/or by the user. One process step in the cannulation is in particular technically implemented by a component of the cannulation robot, e.g. a tool device, specifically configured for said process step and is selected from the group comprising the possible process steps P1, P2, P3 . . . , without this numbering defining a sequential ordering:

P1: Using an accessory kit to perform the cannulation which is selected prior to commencing the automated cannulation based on the registered patient identifier; this selection can have been made previously by means of an optional pick-and-place system of the system for selecting an accessory kit and/or equipping an accessory holder, in particular an accessory box; the accessory kit can have been provided beforehand as a function of the registered patient identifier by an optional sorting apparatus of the system selecting the accessories contained in the accessory kit from an optional storage apparatus of the system for storing accessories; the accessory kit can contain one or more medical accessories, in particular gauze, swabs, adhesive tape; the accessories of this accessory kit can be gathered as a function of the registered patient identifier and/or as a function of patient-specific treatment data derived from the registered patient identifier; the use of this accessory kit by the cannulation robot is a process step of the automated cannulation and can provide for the accessories of the accessory kit to be automatically extracted from predetermined positions of an accessory holder/box, in particular by the appropriate program parameters being selected as a function of the registered patient identifier and suitable for extraction; an optional pick-and-place device of the cannulation robot being in particular used to that end which is configured to extract the accessories out of the accessory holder and/or configured to equip one or more optional tool devices of the cannulation robot;

P2: Spatially fixating a part of the patient's body containing the blood vessel, in particular an arteriovenous fistula; the program parameters of the automated cannulation can be selected here as a function of the registered patient identifier, thus individual to each patient, these program parameters setting beforehand the position or the spacing of one or more optional fixation devices of the cannulation robot based on a previously determined location or on predetermined spacings on the patient's body part so as to achieve suitable fixation; the fixation taking place in the treatment chamber of the cannulation robot in which the patient's body part rests for the at least one ensuing cannulation;

P3: Using stored—in particular in a patient database—patient data in order to determine information on past cannulation process steps in the patient's vasculature (historical data), and preferably define the cannulation to occur, in particular the program parameters thereby used, based on this historical data; such historical data containing in particular the location of one or more of the patient's blood vessels previously measured by an optional measuring device of the cannulation robot for measuring the location and/or dimensions of at least one blood vessel under the patient's skin (vascular structure measuring device), and providing same in particular as patient data; such historical data containing in particular information on the location and condition of further puncture sites on the patient's body which is in particular provided as patient data; the vascular structure measuring device being able to be designed to detect the location and/or dimensions of at least one blood vessel under the patient's skin by means of ultrasound or by means of optical radiation;

P4: Identifying the blood vessel under the patient's skin suitable for the blood withdrawal, in particular selecting a suitable insertion site on the skin for the cannulation of said blood vessel; the program parameters of the automated cannulation can hereby be selected as a function of the registered patient identifier, thus individual to the specific patient, by the cannulation planned for the registered patient being selected on the basis of at least one patient-specific treatment parameter; for example with a patient planned for hemodialysis; a treatment parameter can encode the patient's necessity for hemodialysis; the cannulation of an arteriovenous blood vessel can be planned by evaluating the treatment parameter; same being identified; the identification can for example ensue in the control system by a program-controlled analysis of an image obtained by a vascular structure measuring device;

P5: Disinfecting the skin of the patient's body part containing the blood vessel; the program parameters of the automated cannulation can hereby be selected as a function of the registered patient identifier, thus individual to the patient, by a disinfecting process being specifically selected for the patient's type of skin or skin morphology which is for example characterized by the length of the treatment or the amount and nature of the disinfecting process employed; treatment data specific to the patient can also be considered; a disinfecting device which is optional with the cannulation robot or separate therefrom and equipped to perform the cited function can be used for the cited disinfection; the type of skin or skin morphology of the patient being preferably known in particular as patient data in the patient database;

P6: Physically treating the patient's body part containing the blood vessel in preparation for the cannulation, in particular stemming the blood flow of the body part, applying pressure to the body part, controlling the temperature of the body part, positioning the immobilized body part; the program parameters of the automated cannulation can hereby be selected as a function of the registered patient identifier, thus individual to the specific patient, by drawing on preparation data specific to the planned patient treatment, e.g. hemodialysis, or which can be taken from the patient database as known preparation data; this preparing for the cannulation of the body part being in particular performed by an optionally provided prepping device of the cannulation robot correspondingly configured for this purpose;

P7: Puncturing the blood vessel, in particular an arteriovenous fistula; preferably a first venipuncture and cannulation occurring automatically for withdrawing blood from the blood vessel and a second venipuncture and cannulation occurring automatically for the return of the blood, in particular in the case of hemodialysis; the program parameters of the automated cannulation can hereby be selected as a function of the registered patient identifier, thus individual to the specific patient, by the program parameters defining a patient-dependent motion control for a robotic tool arm optionally provided in the cannulation robot, by means of which a medical accessory such as for instance an injection needle can for example be grasped by the tool arm and positioned on the body part, with the injection needle having been previously selected and prepared specific to the patient; two cannulation robots can be set up for puncturing blood vessels at different parts of the body by, for example, a first cannulation robot being configured for cannulation on an arm and a second cannulation robot being configured for cannulation on a leg; the selection of the appropriate cannulation robot can ensue in patient-specific and/or treatment-specific manner; using one cannulation robot each on both respective arms (legs) is for example also possible.

P8: Withdrawing blood from the cannulated blood vessel and transporting the blood in at least one blood transport device or in at least one sample container; the program parameters of the automated cannulation can hereby be selected as a function of the registered patient identifier, thus individual to the specific patient, by a suitable blood transport device or suitable sample container being preselected as a function of patient-specific treatment data and then utilized in suitable manner by the cannulation robot; the cannulation robot and the control system can be configured thereto by an appropriate selection of the program parameters to provide at least one sample container based on treatment data for the subsequent, preferably automatic and system-controlled, treatment, in particular diagnostics;

P9: The grasping of a cannula by a gripper apparatus of the cannulation robot.

The term "cannulation" refers to a procedure in which a cannula is inserted into the blood vessel in the patient's body part by puncturing the skin and venipuncturing the blood vessel wall so that the distal end of the cannula is disposed in the blood vessel and the proximal end of the cannula is disposed on the outside of the body part so that a fluid connection can be established between the cannula and the blood vessel, by means of which fluid, in particular blood and/or fluid media, can be exchanged via the fluid connection. The "exchange" of fluid in this context means that fluid from the patient's blood circulation is conveyed to an extracorporeal fluid system, i.e. situated external of the patient's body, in particular for fluid storage or fluid conduction, and/or includes conveying fluid from the extracorporeal system into the blood circulation.

Chronically ill patients need regularly repeated vasculature cannulation in order to ensure the necessary treatment. One such chronic illness is kidney failure which leads, among other things, to the loss of the blood's natural purifying function. Technical solutions can be substituted in its place. Hemodialysis devices are extracorporeal filtering units serving as artificial kidneys into which the blood of the patent is conducted in order to be cleansed and treated before being returned to the patient's blood circulation. Blood is normally withdrawn and returned via an artificial subcutaneous connection surgically created between a vein and an artery in an arm or a leg of the patient. This connection can be composed of a section of the patient's own vasculature prepared for same or can consist of an artificial material and is referred to as a fistula or arteriovenous fistula respectively (AV fistula, AVF). The most commonly used permanent vascular access in chronic hemodialysis patients is a native arteriovenous fistula. After the native arteriovenous fistula is placed, it becomes stronger due to the increased blood flow, whereby repeated cannulation for the dialysis treatment becomes easier.

Hemodialysis must be performed regularly, typically a few days apart. This leads to high mechanical stress on the blood vessel or arteriovenous fistula respectively. Different techniques are known to create access to a blood vessel or arteriovenous fistula respectively, these aiming to be as gentle as possible on the vessel over the course of the repeated cannulation. In rope ladder cannulation, a new cannulation site located at a distance from the previous site, e.g. about 2 cm, is sought for each treatment. In this method, the series of punctures are usually started at the lower end of the vessel and then continue upward until reaching the upper end and the process then started again from below. The practitioner must thereby precisely follow the positioning pattern so as to allow the venipunctured vessel sites to heal. In contrast, in the buttonhole technique, a needle is always inserted into the exact same spot at the exact same angle. Over time, a scar tunnel thus develops which continually displaces the thrombus forming in cannulation and thus becomes more resilient. It has been found that buttonhole technique results can be improved if the cannulation is always performed by the same treatment personnel. For this reason, the use of a cannulation robot is particularly advantageous.

Due to the frequency of cannulation with hemodialysis patients, the arteriovenous fistula is subject in general to high stress, independent of the venipuncture technique, same which can lead to changes in the surface of the skin and the condition of the arteriovenous fistula and how they progress. The present invention allows regulated optimizing of the position and/or dimensions of the blood vessel so that in particular an automatic cannulation can be realized gently, quickly and efficiently.

One advantage of the cannulation robot with automatic disinfection machine can additionally be seen in that, in particular when treating chronic illnesses—in particular with hemodialysis patients—, the automated cannulation can reduce the workload of the medical personnel and/or provide a consistently high cannulation precision, whereby in particular treatment quality and/or treatment safety can be increased.

The potential advantages as well as embodiments, further developments or variants of the aspects of the invention cited previously also apply accordingly to the inventive method. Inversely, potential advantages as well as embodiments, further developments or variants of the method also apply accordingly to the preceding aspects of the invention.

As defined by the invention, "configured" refers to an apparatus not only being in principle suited to fulfill a specific function—for instance only after a specific program code has been loaded; i.e. the apparatus programmed, or the apparatus formed in a specific way—, but the apparatus already possesses all the means necessary in order to actually fulfill the function. Preferably, the apparatus is to that end already programmed with a program code for said function and/or already configured and/or arranged and/or exhibits such a configuration thereto that the apparatus actually fulfills the function.

"Treatment of a patient" in the sense of the invention refers to at least one medical; i.e. in particular therapeutic, diagnostic or cosmetic, procedure which effects changes to the body and/or health of the patient or by means of which the state of the patient's health is determined. A treatment is in particular an administration of medicinal products, a cannulation, a blood purification procedure such as dialysis, an operation and/or an examination of the patient.

A "group of treatments" in the sense of the invention can be respective specific operations, therapy for a specific illness, the initial examination of a patient, or a dialysis treatment which in turn can comprise sub-groups, in particular hemodialysis, hemofil-tration, hemodiafiltration, hemoperfusion or peritoneal dialysis treatments.

As defined by the invention, an "individual involved in the treatment" can in particular be understood as an attending person, for instance a physician, or an individual providing treatment support, for instance a nurse. In particular, the patient to be treated can himself also be an individual involved in the treatment or an attending person.

A data processing control device of the detection apparatus and/or the cannulation robot comprises a data processing apparatus.

To be understood by a "data processing apparatus" is an apparatus configured to process data; i.e. in particular to receive data, store received data, read out stored data, transform received and/or stored and/or read data by means of logical and/or mathematical operations, store transformed data, and/or output transformed and/or read data. Preferably, such a data processing device is programmable; i.e. a program code in particular at least partially specifies the method for processing the data and at least part of said program code is modifiable. The program code can to that end be configured to automatically control the disinfecting device and/or automatically control the recording device and/or evaluate the disinfection data.

Preferably, the data processing apparatus is a commercially available microprocessor or computer. Further preferentially, the data processing apparatus comprises at least one data processor—i.e. a central processing unit—, a non-volatile—i.e. in particular permanent—data storage, in particular a hard disk, a read-only memory (ROM) or a drive with a data medium, as well as at least one hardware interface. The data processing apparatus also preferably comprises a volatile electrical data storage, in particular as main memory, preferably a semiconductor memory, in particular with integrated capacitors and/or flip-flops (bistable multivibrators) for data storage, for instance dynamic RAM or static RAM.

In the sense of the invention, a "data storage apparatus" or "data storage device" is an apparatus for storing data. Same is in particular designed to form a data link with a further apparatus, particularly a data processing apparatus, and/or comprises a data link to the further apparatus, wherein data can be transmitted to the data storage apparatus from the further apparatus for storage by means of the data link and/or data can be transmitted from the data storage apparatus to the further apparatus for retrieval. Preferably, the data storage apparatus comprises at least one non-volatile data storage. Also preferably, the data storage apparatus comprises at least one volatile electrical data storage.

A data link connects in particular two data processing units, in particular two data processing devices or apparatus, in a way so as to enable the exchange of data between the units, either unidirectionally or bidirectionally. The data link can be realized in wired or wireless manner, in particular as a radio link. A remote data link connects in particular two data processing units, particularly two data processing devices, disposed at a distance from one another, thus not being component parts of the same device, in particular the same user interface device or the same control system, if the cited devices are realized as separate units. A data link, in particular remote data link, of one device to another device is preferably realized by a direct connection between the two devices or by an indirect connection of the two devices such that a third device is connected between the two devices in order to pass on the data. A remote data link can in particular be realized by a network of computers with which the devices connected by the remote data link are interconnected via the network. The network can be a restricted network, e.g. an intranet, or global network, in particular a WAN and/or the internet.

In the sense of the invention, an "interface device" serves the connection of two units—in particular including systems, apparatus, devices or mechanisms, particularly having such units—, respectively capable of processing signals, in particular information, particularly data, thus in particular sending and/or receiving. An interface device can comprise at least one hardware interface and in particular be integrated into a physical device unit as a component part.

The term "treatment of a laboratory sample" in particular means that a laboratory sample, in particular a sample or a volume of blood, is moved and/or transported and/or examined and/or physically, chemically, biochemically or in some other way modified, in particular as regards its composition.

Preferably, the automatic disinfection machine, in particular a treatment apparatus comprising the automatic disinfection machine, comprises at least one of the following components: a user interface device, with which a user can make at least one data input which is processed by the control device or its program code, and/or with which information can be output to the user, wherein the user interface device can comprise a display, in particular a touchscreen, speaker and/or input device such as e.g. a keyboard; a housing, into which the control device, treatment chamber, disinfecting device and/or the recording device is/are integrated, wherein the housing can comprise an opening or a doorway device providing access to the treatment chamber in order to receive the user's body part; a base, in particular a supporting frame bearing the components of the automatic disinfection machine or at least one of said components; a power supply system for supplying power to the electrical components of the automatic disinfection machine; a communication device for exchanging data with an external data processing apparatus, in particular via remote data link.

The invention further relates to an automatic disinfection machine for controlling the disinfection of a patient's skin which comprises:—a treatment chamber for accommodating the part of the body with the skin to be disinfected:—a recording device for recording the disinfection result on the skin in the form of disinfection data, —a data processing control device for controlling the recording device; wherein the control device is to that end designed to record the disinfection result from a section of skin in the form of disinfection data by controlling the recording device. Disinfection is controlled in such an automatic disinfection machine, in particular without the performance of same, wherein the disinfection was previously performed automatically by means of a separate disinfecting device or manually. Moreover, the automatic disinfection machine can also be configured as a disinfection control pursuant to the present described configuration options of the automatic disinfection machine with controlled disinfection function.

The invention further relates to an automatic disinfection machine for disinfecting the skin of a patient which comprises:—a treatment chamber for accommodating the part of the body with the skin to be disinfected, —an electrically controllable disinfecting device for disinfecting the skin, —a data processing control device for controlling the disinfecting device, wherein the control device is to that end designed to perform the disinfection of the skin by controlling the disinfecting device. Disinfection of the skin is performed with such an automatic disinfection machine, in particular without its control. Moreover, this automatic disinfection machine can also be configured to disinfect pursuant to the present described configuration options of the automatic disinfection machine with controlled disinfection function.

The invention further relates to a data processing system comprising an automatic disinfection machine according to the present description and/or a treatment apparatus comprising said automatic disinfection machine, in particular a cannulation robot, and at least one external data processing apparatus networked with the automatic disinfection machine and/or the treatment apparatus for the exchange of data, in particular over a data link or a remote data link. The system can further comprise a data storage apparatus as a component, same being networked to at least one other system component for exchanging data. The data storage apparatus can contain a patient database in which patient data is stored and able to be retrieved. The system can to that end be designed to generate and store certificate data, in particular save it to the data storage apparatus.

The invention further relates to a method for the controlled disinfection of a section of a patient's skin, in particular a method for operating an automatic disinfection machine, in particular an automatic disinfection machine in accordance with the invention, comprising the steps of:—automatically disinfecting the skin section by means of controlling an electrically controllable disinfecting device; —recording the disinfection of the skin section in the form of disinfection data by means of controlling a recording device.

The invention further relates to a method for the automatic cannulation of a blood vessel under the skin of a patient's body part, in particular a method for operating a cannulation robot, particularly a cannulation robot in accordance with the invention, comprising the steps of the inventive method for automatically disinfecting the skin section, and comprising the step(s) of:—Automatic cannulation of the disinfected skin section; —optionally: Performing said cannulation within a predetermined limited interval of time.

Further application possibilities of a method according to the invention can be deduced from the description of the inventive automatic disinfection machine and/or cannulation robot and their configurations.

Further advantages, features and possible applications of the present invention are yielded by the following detailed description of at least one example embodiment and/or by the figures. Unless otherwise described or contextually indicated otherwise, the same reference numerals are substantially used to identify equivalent components in the embodiments. The figures show the following example embodiments of the invention:

FIGS. 1 to 3 in each case show a side view of example embodiments of the inventive automatic disinfection machine according to the first preferential embodiment in which a measurement characterizing the disinfection quality is made on the disinfected section of skin.

FIGS. 4 and 5 in each case show a side view of example embodiments of the inventive automatic disinfection machine according to the second preferential embodiment, in which a measurement characterizing the disinfection quality is made on the recording device, but in particular not on the skin section.

Figure 1:
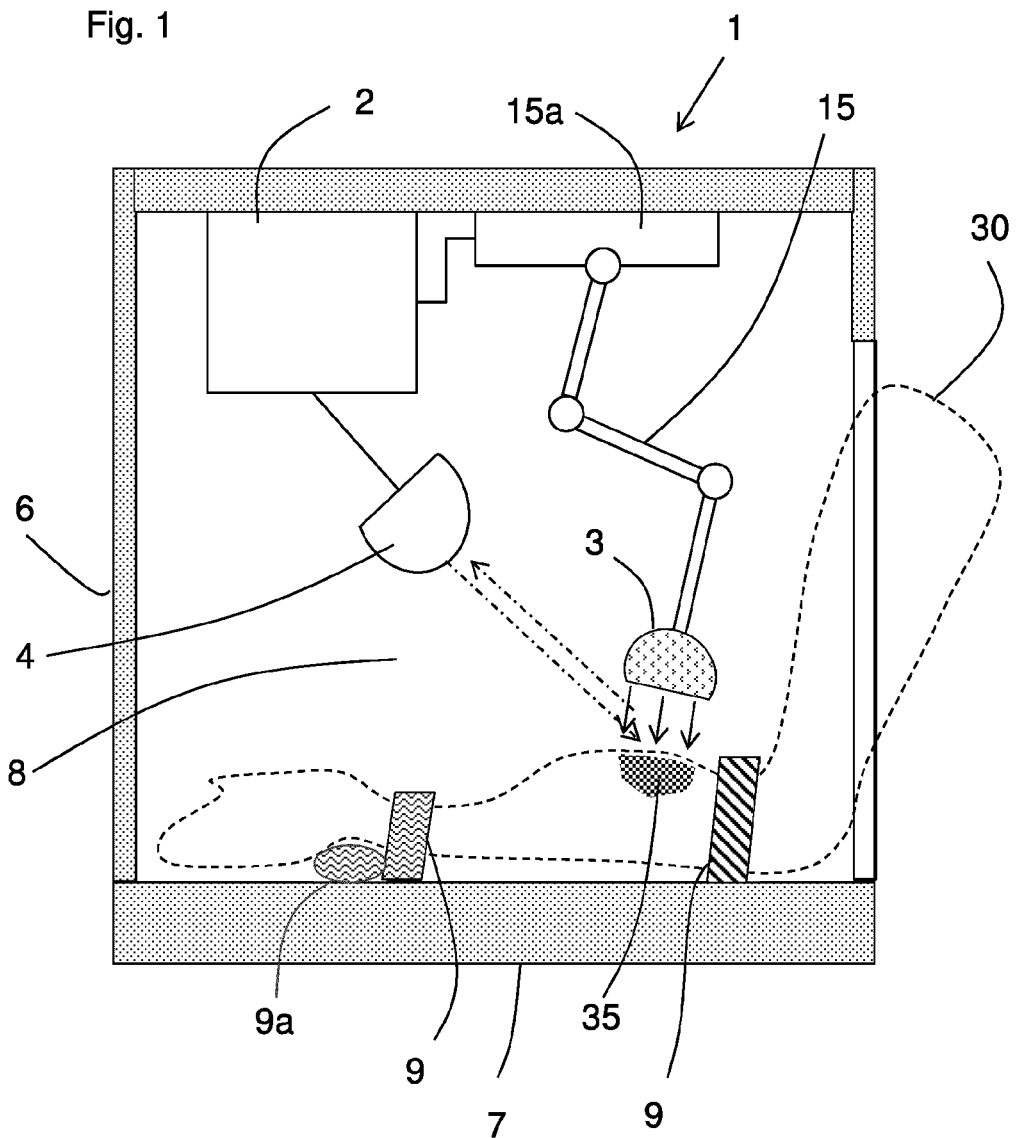

FIG. 1 shows the automatic disinfection machine 1 as configured for the controlled disinfection of the skin of a patient. The automatic disinfection machine 1 comprises a treatment chamber 8 for accommodating the body part 30, here a forearm 30, with the skin to be disinfected. The automatic disinfection machine 1 comprises an electrically controllable disinfecting device 3 for disinfecting the skin, a recording device 4 for recording the disinfection of the skin in the form of disinfection data, a data processing control device 2 for controlling the disinfecting device and the recording device. The control device 2 is thereby designed to perform the disinfection of the skin by controlling the disinfecting device and to record the disinfection of skin section 35 of the skin in the form of disinfection data by controlling the recording device. A measurement which characterizes the disinfection quality is additionally taken of the disinfected skin section 35 subsequent the automatic disinfection.

The disinfecting device 3 can hereby be a spray device for spraying a liquid disinfectant onto the skin and/or comprise a radiation device, in particular a radiation device emitting UV-C radiation, which irradiates the skin section 35. This process is illustrated by the continuous arrows 35 pointing toward the skin section as disposed perpendicular to said skin section. The recording device 4 can comprise an image capture device and an applicable beam guidance so as to record a digital image of the disinfected skin section in the form of disinfection data. This process is illustrated by the broken arrows. Active colorants can be disposed on the skin which reveal the existence of sufficient disinfecting action under optical measurement. The data processing device of the control device determines from the image that surface portion of the skin section which is sufficiently wetted by the liquid disinfectant or sufficiently irradiated by the radiation device. The control device's digital image evaluation can thereto draw on thresholds in order to allocate pixels of the image having e.g. sufficient brightness above the threshold to the sufficiently wetted surface portion. The surface sufficiently encompassed by the disinfecting action divided by the total area of the skin section can be used as the disinfection variable characterizing the disinfection quality.

The disinfecting device 3 is held at a movable retention device 15, which is configured here as movable articulated arm 15, moved by means of a drive and control unit 15a. If the automatic disinfection machine 1 is a component part of a treatment device, the disinfecting device 3 and/or the recording device 4 can be a module able to be mounted on an articulated arm 15 of the treatment apparatus and thus movable.

The automatic disinfection machine 1 further comprises a base 7 and a frame 6 which support the component parts of the automatic disinfection machine. A fixation device 9 with cushion support 9a is fastened to the base 7, by means of which the body part 30 is immobilized in the treatment chamber 8. The disinfection and the recording is thereby rendered more precise and thus safer.

Figure 2:
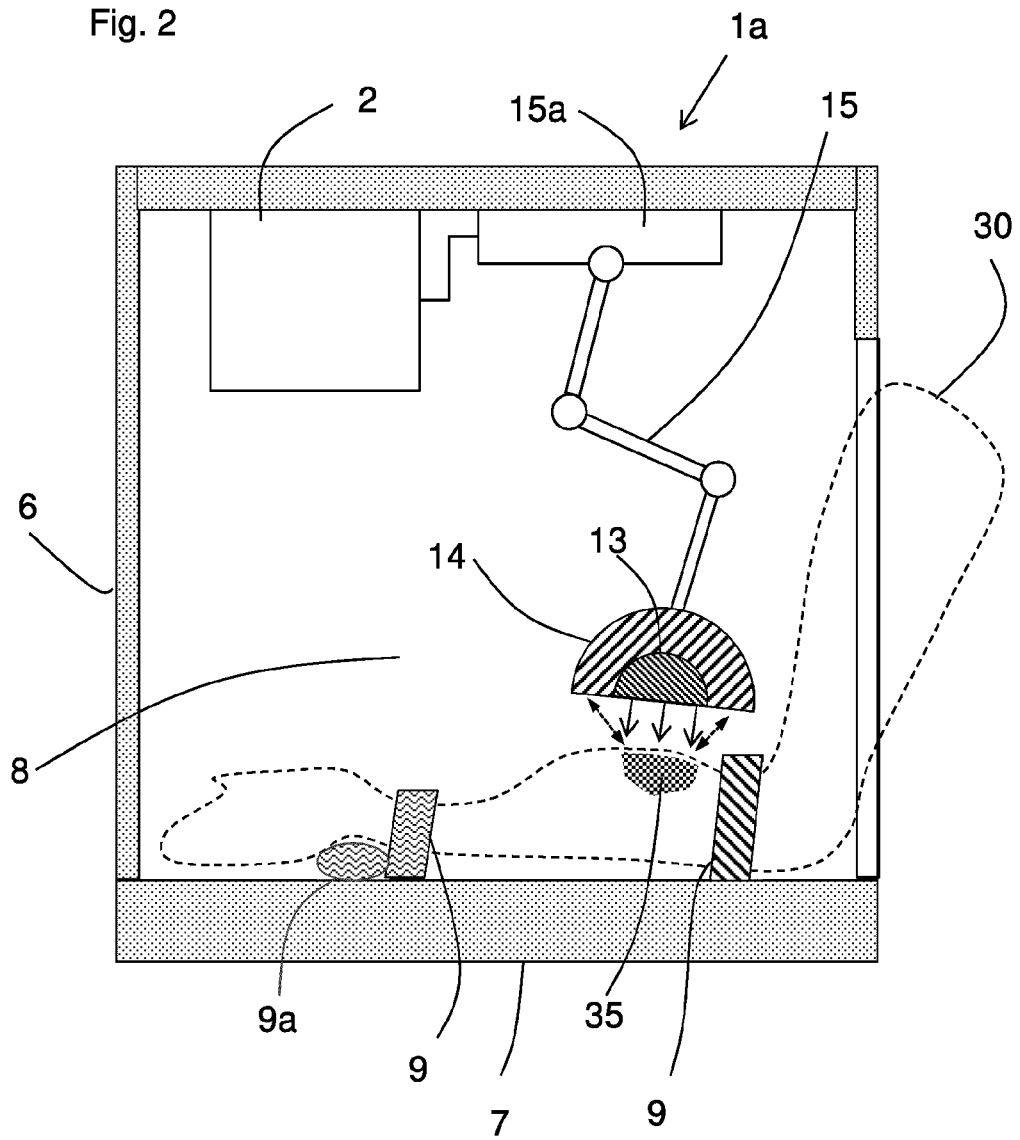

FIG. 2 shows an automatic disinfection machine 1a configured similar to that of FIG. 1. In automatic disinfection machine 1a, the recording device 14 is arranged on the same retention device 15 bearing disinfecting device 13, which can correspond to disinfecting device 3. The recording device 14 and the disinfecting device 13 are in particular arranged symmetrically and preferably concentrically about the axis perpendicular to the skin section, whereby the axis runs parallel to the three solid parallel arrows and through the center of the skin section. The disinfecting action (radiation, liquid disinfectant streams) is applied perpendicular to the skin section, the image is acquired here by a plurality of imaging sensors (not shown) disposed at an angle α to the vertical, as illustrated by the double arrows. The recording device 14 can additionally comprise light sources for illuminating the skin section, which can likewise be arranged concentrically.

Figure 3:
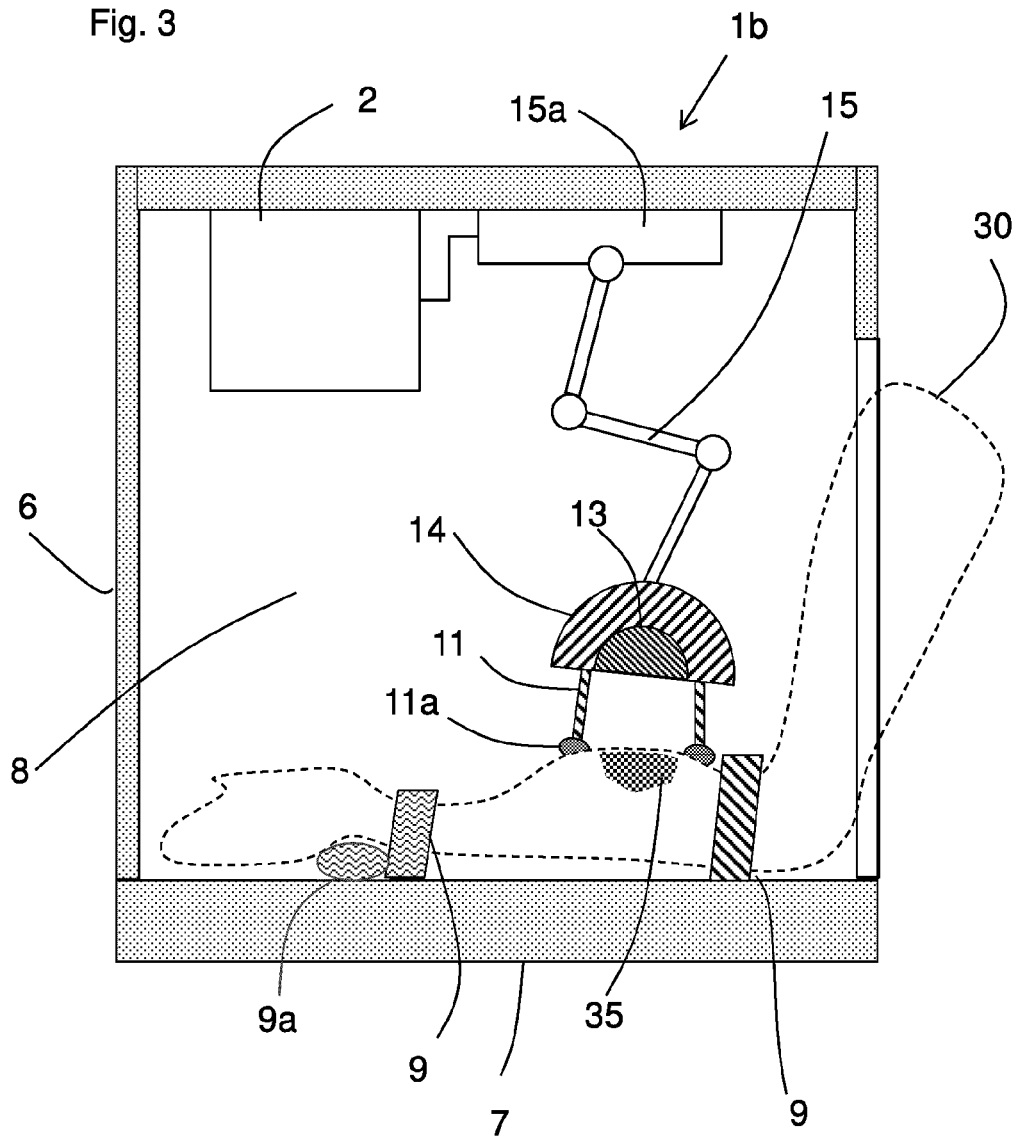

FIG. 3 shows an automatic disinfection machine 1b configured similar to that of FIG. 2. The automatic disinfection machine 1b comprises a skin manipulating device 11 which is arranged here on the disinfecting device 13. The skin section 35 can be moved by the skin manipulating device while the body part 30 comprising the skin section 30 is fixed. The skin manipulating device 11 comprises two movable contact sections 11a with which the skin is contacted and stretched by means of a friction-based transmission of power by the skin manipulating device 11. The contact section 11a is affixed to the movable and deflectable arm 11 of the skin manipulating device. The skin of skin section 35 is stretched here prior to disinfection by the skin manipulating device 11. This thereby achieves a smoothening of the skin and thus a uniform disinfecting action. This tautening of the skin section is likewise realized during the recording of the disinfection data.

Figure 4:
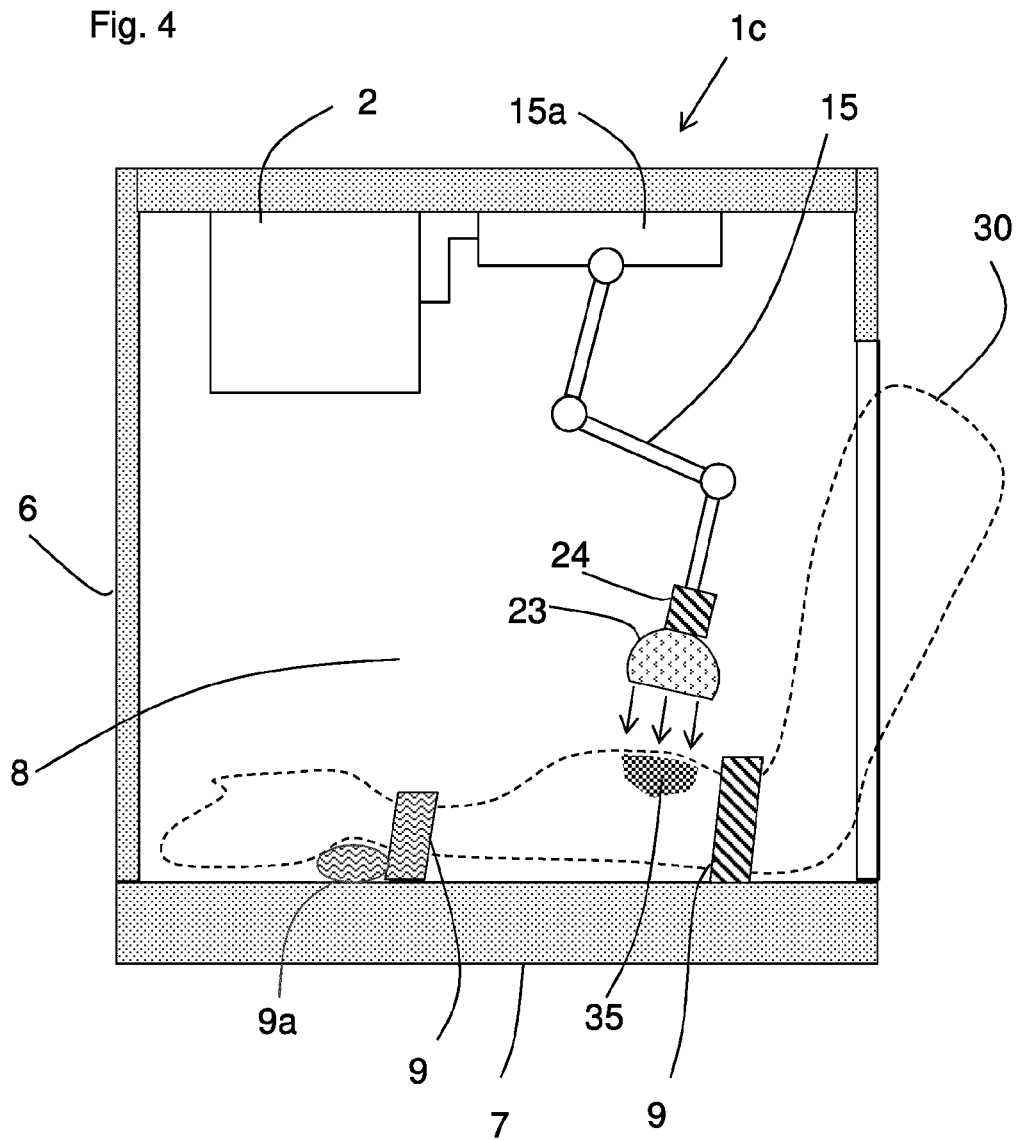

FIG. 4 shows the automatic disinfection machine 1c according to the second preferential embodiment in which a measurement characterizing the disinfection quality is made on the recording device 24, in particular, however, not on skin section 35. The recording device 24 is directly arranged on the disinfecting device 23. It records for example by means of sensors the power input of an electrically operated pump (not shown) via which the disinfectant is sprayed onto the skin as disinfection data.

Figure 5:
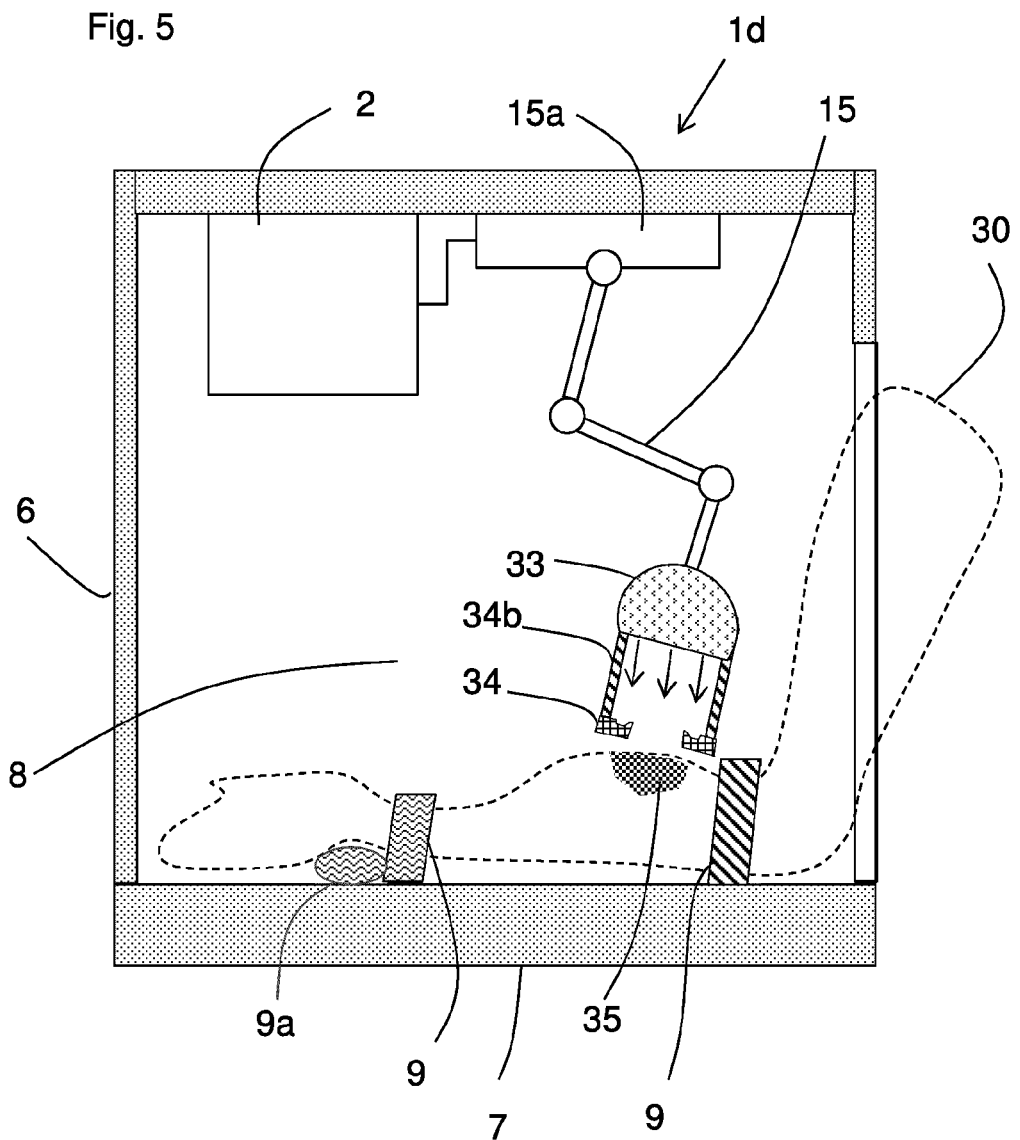

FIG. 5 shows the automatic disinfection machine 1d according to the second preferential embodiment in which a measurement characterizing the disinfection quality is made on the recording device 34, in particular, however, not on skin section 35. The recording device 34 is connected here to the disinfecting device 33 by means of a mounting 34b. The sensors of the recording device 34, depicted as structures partially projecting into the range of the disinfection streams, measure the disinfecting action by, for example, capacitively measuring the formation of a liquid disinfectant coating thickness on the sensor measuring area or by measuring irradiating radiation intensity by photoelectric cell. The disinfecting action is integrated over the time of the effect and used by control device 2 to generate the disinfection variable.

Figure 6:
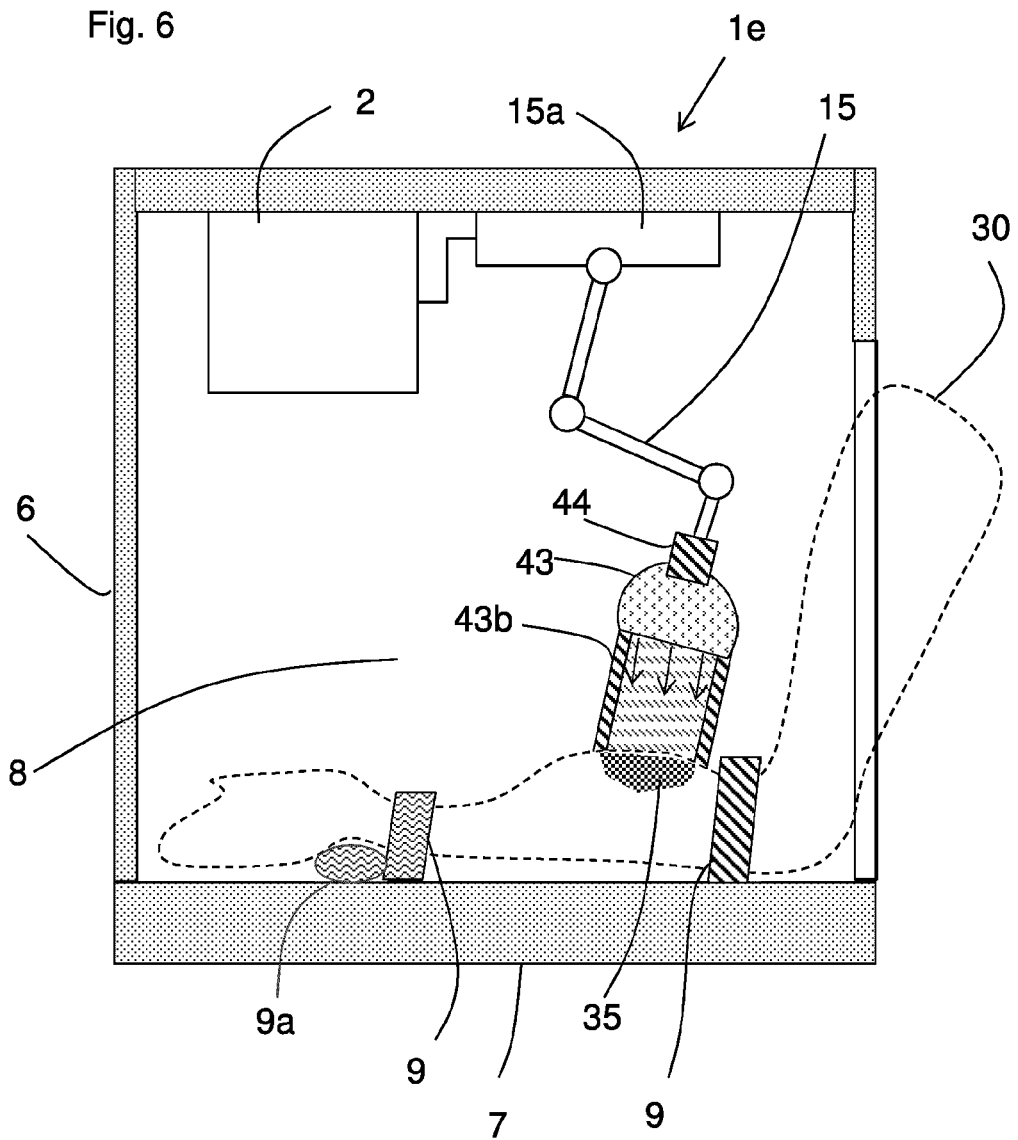
FIG. 6 shows a side view of the inventive automatic disinfection machine according to one example embodiment having a compartment for exposing the skin section to a disinfecting gas or plasma.

FIG. 6 shows an automatic disinfection machine 1e configured similar to that of FIG. 4. The disinfecting device 43 here comprises a compartment device 43b with an opening facing toward the skin section 35 which closes when placed on the skin and defines the skin section 35. The thus closed interior is filled with a disinfecting gas or a disinfecting cold plasma. The recording device 44 can be designed to measure a gas concentration or a plasma concentration.

Figure 7:
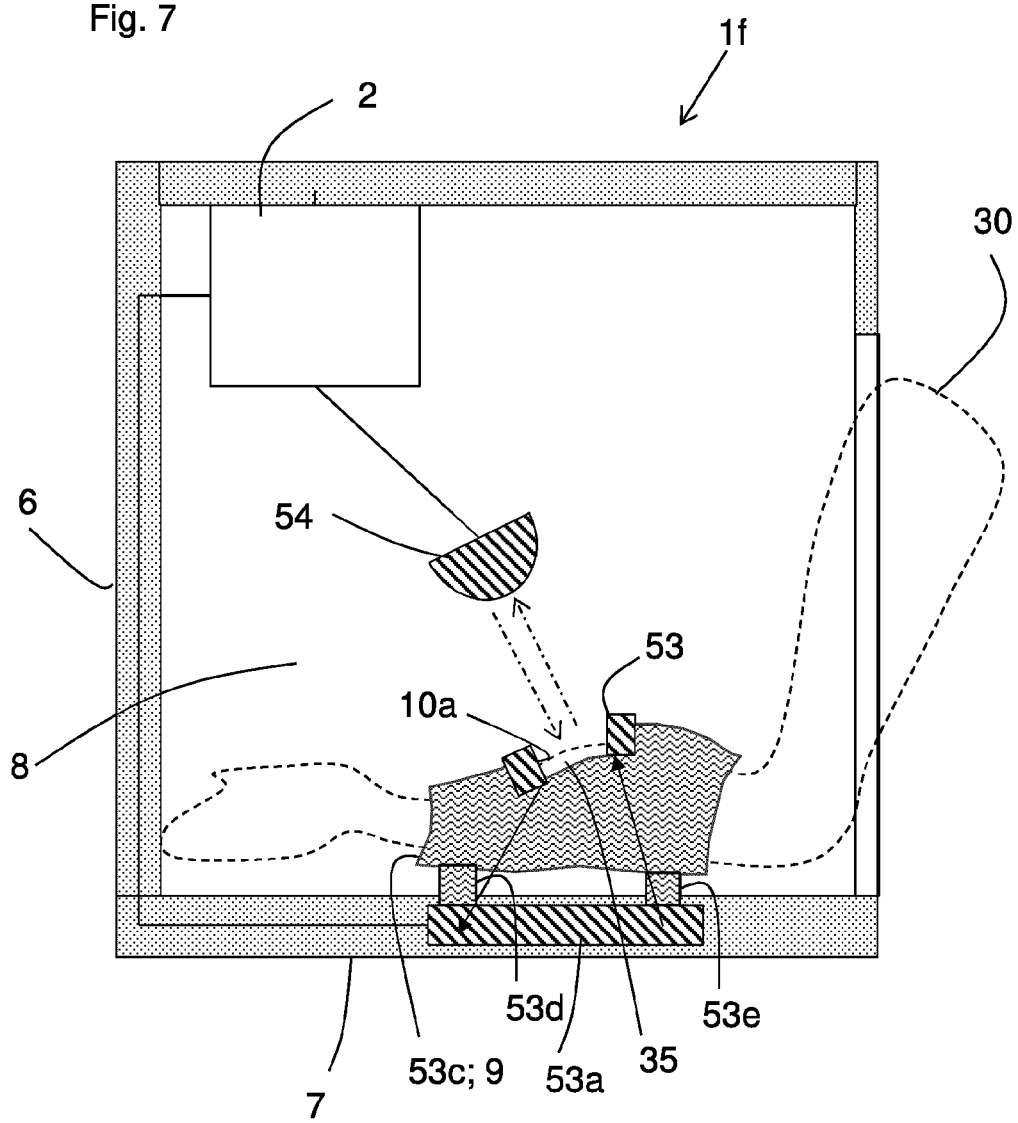
FIG. 7 shows a side view of the inventive automatic disinfection machine according to the first preferential embodiment in an example embodiment in which the disinfecting device is integrated into the fixation device which immobilizes the body part in the treatment chamber.

FIG. 7 shows the automatic disinfection machine 1f configured for the controlled disinfection of the skin of a patient. The automatic disinfection machine 1f comprises a recording device 54 configured as an image capture device which is designed to capture one or more images of the skin section 35 to be and/or already disinfected by means of the control device 2. A fixation device 9 immobilizes the patient's body part in the treatment chamber. The fixation device comprises a body part cuff, here an arm cuff, fastened to the base 7 which is connected to the base by sections 53d and 53e. The arm cuff has a window 10a via which the skin section 35 is accessible for the optical measurement and the application of the disinfectant. The disinfecting device 53 is arranged at the edge of the window 10a here and connected to the arm cuff of the fixation device 9. The arm cuff hereby in particular serves as a retention device 53c for the disinfecting device 53. By means of a pumping and control unit 53a arranged on the automatic disinfection machine which is fluidly connected to the spray device of the disinfecting device 53 by a (not shown) fluid channel, the skin section is efficiently disinfected from the immediate proximity while the spatial area above the skin section 35 remains free so that in particular the measuring by means of the image capture device 54 can be optimally realized.

Figure 8:
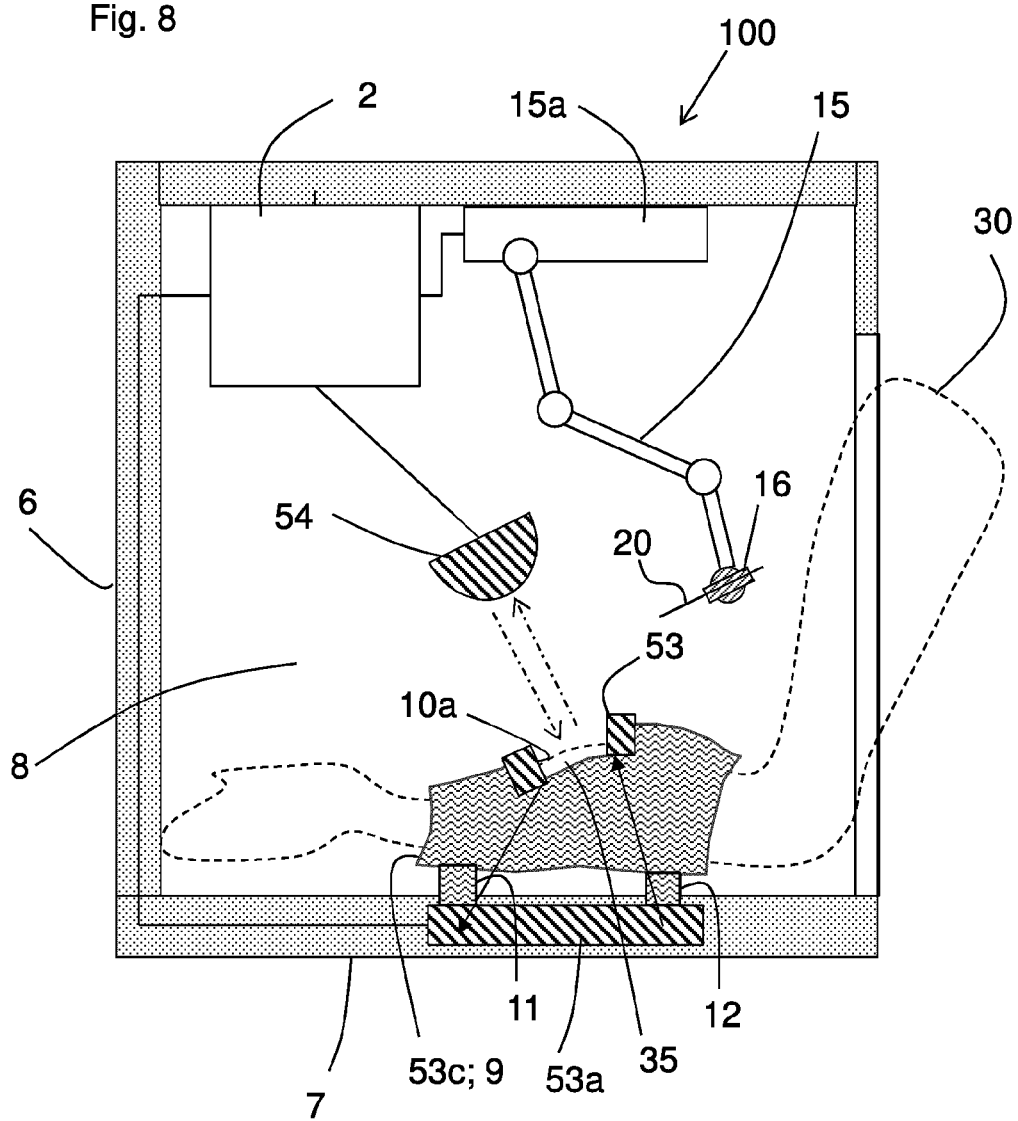
FIG. 8 shows a side view of an inventive cannulation robot according to one example embodiment comprising the automatic disinfection machine according to FIG. 7.

FIG. 8 shows the cannulation robot 100 comprising the automatic disinfection machine 1f according to FIG. 7. The cannulation robot additionally comprises a movable articulated arm provided with a cannula holder 16 and supporting the cannula 20 which is actuated by means of the drive and control unit 15a. The control device 2 is designed here to automatically select a subcutaneous blood vessel for the cannulation, locate a suitable puncture site in said blood vessel, define the intended puncture site as the center of the skin section 35 to be disinfected, automatically perform the disinfection of the skin section by means of disinfecting device 53, automatically record the disinfection by generating and storing disinfection data via the recording device 54, automatically perform a cannulation at the disinfected puncture site—and for example also record the cannulation via the recording device 54 by generating and storing treatment data, and in particular use the disinfection data and the treatment data to generate certificate data. Said certificate data forms a certificate or a protocol which can be part of an electronic physician's report and which is stored as patient data in a patient database as part of an electronic patient file.

Figure 9:
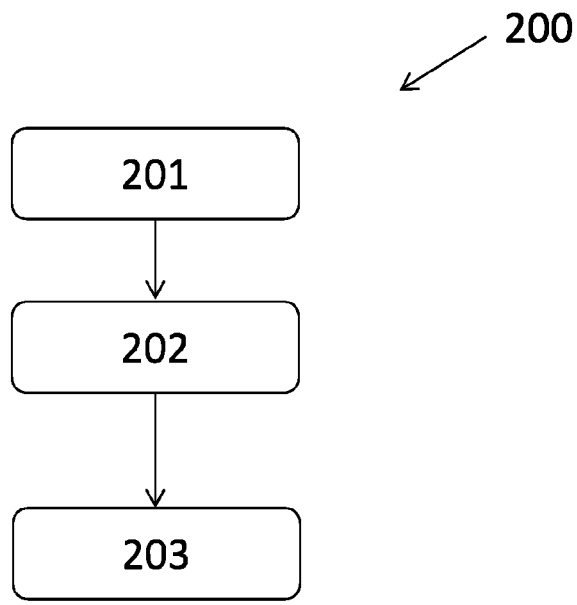
FIG. 9 shows the method according to the invention for the controlled disinfection of the skin of a patient according to one example embodiment.

FIG. 9 shows the inventive method 200 for the controlled disinfection of the skin of a patient according to one example embodiment comprising the steps:
(201) automatic disinfecting of the skin section by means of controlling of an electrically controllable disinfecting device;
(202) recording the disinfection of the skin section and
(203) generating disinfection data by means of controlling a recording device.

The invention claimed is:

1. An automatic disinfection machine for the controlled disinfection of the skin of a patient, comprising:
a treatment chamber for accommodating the body part with the skin to be disinfected,
an electrically controllable disinfecting device for disinfecting the skin,
a recording device for recording the disinfection of the skin in the form of disinfection data,
a data processing control device for controlling the disinfecting device and the recording device,
wherein the control device is designed to effect the disinfection of the skin by controlling the disinfecting device, the control device is designed to record the disinfection of a skin section of the skin in the form of disinfection data by controlling the recording device, and
the disinfection machine further comprises a skin manipulating device comprising at least two movable arms, on each of which a contact section is arranged, and which is configured to stretch the skin section by contacting the contact sections with the skin section and by means of a friction-based transmission of power.

2. The automatic disinfection machine according to claim 1, wherein the recording device comprises a sensor device by means of which a measurement characterizing the disinfection quality can be made on the skin section.

3. The automatic disinfection machine according to claim 2, wherein the sensor device is an image capture device, and wherein the control device is designed to record at least one image of the skin section by means of said image capture device in the form of image data forming a component part of the disinfection data.

4. The automatic disinfection machine according to claim 1, wherein the disinfecting device comprises a spray device configured to deposit a liquid disinfectant directed onto the skin section.

5. The automatic disinfection machine according to claim 1, wherein the recording device comprises a sensor device by means of which a measurement characterizing the disinfection quality can be made on the recording device.

6. The automatic disinfection machine according to claim 5, wherein the recording device comprises a detection device by means of which at least one disinfection parameter characterizing the operation of the disinfecting device is queried at least once during the automatic disinfection and saved.

7. The automatic disinfection machine according to claim 6, wherein the disinfection parameter characterizes the operations executed, the energy consumed, an output of the disinfecting device or the power input during the disinfection.

8. The automatic disinfection machine according to claim 6, wherein the control device is designed to re-disinfect the same section of skin as a function of the disinfection variable by controlling the disinfecting device.

9. The automatic disinfection machine according to claim 5, wherein the sensor device comprises at least one sensor controlled by the control device which is arranged during the realization of the disinfection by the disinfecting device between the disinfecting device and the skin of the patient so as to measure the disinfecting action.

10. The automatic disinfection machine according to claim 1, wherein the automatic disinfection machine is designed for effect on a skin section which is defined by the disinfecting action locally applied to the skin and/or by a locally limited recording area or by a local limited analysis area of the skin to be disinfected.

11. The automatic disinfection machine according to claim 1, wherein the control device is designed to determine whether a performed disinfection is acceptable on the basis of one criterion, wherein the criterion allows for the comparison of a disinfection variable to at least one predetermined reference value.

12. The automatic disinfection machine according to claim 1, wherein the control device is designed to use the disinfection data or data derived therefrom to form certificate data certifying and storing the disinfection as performed.

13. A treatment apparatus for treating a skin section of a patient, wherein the treatment apparatus comprises an automatic disinfection machine for the controlled disinfection of the skin section of the patient, the automatic disinfection machine comprising:
a treatment chamber for accommodating the body part having the skin section to be disinfected,
an electrically controllable disinfecting device for disinfecting the skin section,
a recording device for recording the disinfection of the skin section in the form of disinfection data, a data processing control device for controlling the disinfecting device and the recording device, wherein the control device is designed to effect the disinfection of the skin section by controlling the disinfecting device, the control device is designed to record the disinfection of the skin section of the skin in the form of disinfection data by controlling the recording device, the disinfection machine further comprises a skin manipulating device comprising at least two movable arms, on each of which a contact section is arranged, and the skin manipulating device is configured to stretch the skin section by contacting the contact sections with the skin section and by means of a friction-based transmission of power.

14. A treatment apparatus according to claim 13, further comprising a cannulation robot for the automatic cannulation of a blood vessel located under the skin section, after disinfection.

15. A method for the controlled disinfection of a skin section of a patient, including a method for operating an automatic disinfection machine for the controlled disinfection of the skin section of the patient, wherein the automatic disinfection machine comprises:

a treatment chamber for accommodating a body part with the section skin to be disinfected, an electrically controllable disinfecting device for disinfecting the skin section, a recording device for recording the disinfection of the skin section in the form of disinfection data, and a data processing control device for controlling the disinfecting device and the recording device, wherein the control device is designed to effect the disinfection of the skin section by controlling the disinfecting device, the control device is designed to record the disinfection of the skin section in the form of disinfection data, by controlling the recording device, the disinfection machine further comprises a skin manipulating device comprising at least two movable arms, on each of which a contact section is arranged, the skin manipulating device is configured to stretch the skin section by contacting the contact sections with the skin section and by means of a friction-based transmission of power, and the method comprises the steps of:

automatically disinfecting the skin section by means of controlling the electrically controllable disinfecting device;

recording the disinfection of the skin section in the form of disinfection data by means of controlling the recording device; and automatically controlling the skin manipulating device, to stretch the skin section while performing the step of automatically disinfecting the skin section.

* * * * *